(12) United States Patent
Bates

(10) Patent No.: US 7,241,583 B2
(45) Date of Patent: Jul. 10, 2007

(54) TRL1 AS AN ANTIFUNGAL TARGET

(75) Inventor: Steven Bates, Westhill (GB)

(73) Assignee: Oxford Glycosciences (UK) Ltd, Slough, Berkshire (GB)

( * ) Notice: Subject to any disclaimer, the term of this patent is extended or adjusted under 35 U.S.C. 154(b) by 0 days.

(21) Appl. No.: 10/537,581

(22) PCT Filed: Dec. 9, 2003

(86) PCT No.: PCT/GB03/05358

§ 371 (c)(1),
(2), (4) Date: Oct. 7, 2005

(87) PCT Pub. No.: WO2004/053145

PCT Pub. Date: Jun. 24, 2004

(65) Prior Publication Data

US 2006/0094070 A1    May 4, 2006

(30) Foreign Application Priority Data

Dec. 9, 2002    (GB) .................................. 0228704.3

(51) Int. Cl.
*G01N 33/53* (2006.01)
(52) U.S. Cl. ...................................... 435/7.6
(58) Field of Classification Search .................. None
See application file for complete search history.

(56) References Cited

FOREIGN PATENT DOCUMENTS

WO    WO 02/02784    1/2002

OTHER PUBLICATIONS

Belford et al. J. Biol. Chem. 1993;268:2444-2450.*
Wood,V., et al., The genome sequence of Schizosaccharomyces pombe, 2002, Nature, 415 (6874); pp. 871-880.
Giaever, G et al., Functional profiling of the Saccharomyces cerevisiae genome, 2002, Nature, 418(6896): 387-391.
Spaltmann, F, et al., Computer-aided target selection-prioritizing targets for antifungal drug discovery, 1999, Drug Discovery Today, 4: pp. 17-26.
Westaway, SK., et al., Structure and Function of the Yeast tRNA Ligase Gene*, 1988, J. Biol. Chem., 263(7): pp. 3171-3176.
Baymiller, J., et al., Isolation and sequence of the t-RNA ligase-encoding gene of *Candida albicans*, 1994, Gene (Amsterdam), 142: pp. 129-134.
Phizicky, EM., et al., Yeast tRNA Ligase Mutants Are Nonviable and Accumulate tRNA Splicing Intermediates*, 1992, J. Biol. Chem., 267(7): pp. 4577-4582.

* cited by examiner

*Primary Examiner*—Ralph Gitomer
*Assistant Examiner*—Bin Shen
(74) *Attorney, Agent, or Firm*—Klauber & Jackson

(57) ABSTRACT

The present invention relates to a novel antifungal target, tRNA ligase (TRL1), screening methods for TRL1 inhibitors and their use as antifungal compounds, pharmaceutical compositions containing them and their use in medicine, specifically in the treatment of an individual susceptible to or suffering from an anti-fungal infection. In particular the compounds find use in the treatment of topical or mucosal (e.g. thrush and vaginal candidiasis) fungal infections, e.g. caused by fungus of the *Candida* species, and for systemic infections, e.g. caused by fungi of *Candida* and *Aspergillus* species, such as but not limited to *C. albicans, Aspergillus flavus* or *Aspergillus fumigatus*.

2 Claims, No Drawings

SEQUENCE LISTING

<160> NUMBER OF SEQ ID NOS: 2

<210> SEQ ID NO 1
<211> LENGTH: 36
<212> TYPE: DNA
<213> ORGANISM: Homo sapiens

<400> SEQUENCE: 1
taatacgact cactataggg tcaatggtga agtggc         36

```
<210> SEQ ID NO 2
<211> LENGTH: 18
<212> TYPE: DNA
<213> ORGANISM: Homo sapiens

<400> SEQUENCE: 2
ggggtcaacc gggaatcg                                                 18
```

TRL1 AS AN ANTIFUNGAL TARGET

CROSS REFERENCE TO RELATED APPLICATIONS

The present application is a National Stage Application claiming the priority of co-pending PCT Application No. PCT/GB2003/005358 filed Dec. 9, 2003, which in turn, claims priority from Great Britain Application Serial No. 0228704.3 filed Dec. 9, 2002. Applicants claim the benefits of 35 U.S.C. § 120 as to the PCT application and priority under 35 U.S.C. § 119 as to the said Great Britain application, and the entire disclosures of both applications are incorporated herein by reference in their entireties.

The present invention relates to a novel antifungal target, tRNA ligase (TRL1), screening methods for TRL1 inhibitors and their use as antifungal compounds, pharmaceutical compositions containing them and their use in medicine, specifically in the treatment of an individual susceptible to or suffering from an anti-fungal infection. In particular the compounds find use in the treatment of topical or mucosal (e.g. thrush and vaginal candidiasis) fungal infections, e.g. caused by fungus of the *Candida* species, and for systemic infections, e.g. caused by fungi of *Candida* and *Aspergillus* species, such as but not limited to *C. albicans, Aspergillus flavus* or *Aspergillus fumigatus*.

INTRODUCTION

Fungal Pathogens

Two major fungal pathogens are those of the *Candida* species, such as but not limited to, *C. albicans*, and those of the *Aspergillus* species, such as but not limited to, *Aspergillus flavus* or *Aspergillus fumigatus*.

Fungal infections can affect humans and animals. Generally, fungal infections occur as a result of opportunistic infection of a weakened or immune-suppressed individual and these can include infections of the joints and skin. The yeast *Candida albicans* (*C. albicans*) is one of the most pervasive fungal pathogens in humans. It is the cause of an increasing financial and logistic burden on the medical care system and its providers. Although *C. albicans* is a member of the normal flora of the mucous membranes in the respiratory, gastrointestinal, and female genital tracts, it may gain dominance in such locations (e.g. upon treatment with antibacterial antibiotics, in patients with diabetes or in patients using corticosteroids) and be associated with pathologic conditions. In addition, almost all HIV-positive individuals suffer from a *Candida* infection prior to the onset of developing full-blown AIDS. The incidence of life-threatening fungal infections has increased dramatically as the population of immunocompromised individuals (including cancer, organ transplant and AIDS patients) has increased. Present therapeutic options for the treatment of these infections are limited and thus there is a need for new anti-fungal compounds with novel mechanisms of action for use in treating or preventing such fungal infections.

Antifungal drug development often relies on the screening of a large number of compounds before one or more lead compounds are found that are effective against the target fungi. Thus, it is critical for the development of these screens to define proteins essential for survival or growth of the target fungi and to discover means of purifying or producing such proteins. Thus, there is a need in the art to identify essential fungal structural or functional gene products that can serve as targets for drug intervention, and for methods for identifying useful anti-fungal agents that impair the function of these essential fungal gene products, and for compositions that can be used to treat fungal infections by preventing or inhibiting the growth of, and preferentially killing, the fungi.

Identification of "Essential" Genes

Varying definitions are used in the art for what constitutes an essential gene, but the term is most frequently applied to those genes necessary for growth on rich medium. This variation in the art can be misleading and restrictive in terms of identifying gene products that constitute good antifungal targets. A significant amount of *C. albicans* genomic sequence information is available in both public and private (Incyte Genomics Inc.) databases. This can be combined with genomic sequence data from other organisms (The yeast genome directory, 1997, Nature, 387(6632 Suppl):5; Wood V, et al, 2002, Nature, 415(6874):871–80) and with supporting data such as the functional profiling of the *Saccharomyces cerevisiae* genome (Giaever G, et al, 2002, Nature, 418(6896):387–91). This bioinformatics driven approach has allowed the prediction of genes that may be essential in *C. albicans* (Spaltmann F, et al, 1999, Drug Discovery Today, 4:17–26). However, even for relatively closely related organisms such as *Saccharomyces cerevisiae* and *C. albicans*, there are significant differences that make such in silico predictions unreliable. For example, CET1 and CDC25 are not essential in *C. albicans* despite being essential in *Saccharomyces cerevisiae* (Enloe B, et al, 2000, J Bacteriol, October, 182:20, 5730–6; Dunyak D S, et al., 2002, 6th SM Conference on *Candida* and Candidiasis).

There are several strategies for identifying essential genes in *C. albicans* by practical methodology. Negative approaches rely on the inability to generate a strain that contains a disrupted functional target gene. The majority of genes characterised in this way rely on variations of the URA blaster method (Fonzi W A & Irwin M Y, 1993, Genetics, 134:717–728). These techniques can be highly effective for analysing individual genes, but they may not be completely reliable. CET1 was incorrectly reported to be essential in *C. albicans* because viable homozygous mutants could not be recovered using the URA blaster method (Pei, et al, 2001). However it has subsequently been shown not to be essential (Dunyak, et al, 2002). Positive approaches control the expression of the target gene either indirectly, such as using antisense RNA (De Backer M D, et al, 2001, Nat. Biotechnol., March, 19:3, 235–41), or directly such as promoter replacement with inducible promoters such as MRP1 and Tet (Munro C A, et al, 2001, Mol. Microbiol., March 39:5 1414–26; Nakayama H, et al, 2000, Infect. Immun., December 68:12 6712–9).

Genome wide identification of essential genes has not been successfully applied to *C. albicans* for several reasons. These include that *C. albicans* is a diploid organism, is not capable of mating under normal circumstances, and that there are few functional transposable elements. Attempts to overcome these issues by using antisense RNA and promoter interference have had limited success (De Backer et al, 2001). Therefore there is a need in the art for validated essential genes of fungal species, in particular the *Candida* species, that can be used as targets for the development of new antifungal compounds.

TRNA Ligase

TRNA ligase (TRL1) E.C. 6.5.1.3 is one of the two proteins required for splicing of precursor tRNA molecules containing introns (Baymiller J, et al, 1994, Gene, 142, 129–134). It performs the ligation of the two tRNA halves in an ATP-dependent reaction, e.g. ATP+ {ribonucleotide}$_N$+{ribonucleotide}$_M$=AMP+diphosphate+

{ribonucleotide}$_{N+M}$. The TRL1 enzyme is encoded by the TRL1 gene (RLG1/LIG1) and details for the fungal enzyme are provided under Accession number: P43075 in the Swiss Prot database; CA4962 in the Institut Pasteur *Candida* database which is cross-referenced to the Stanford open reading frame (ORF) orf6.7649. Synonyms for TRL1 include RNA ligase (ATP), Polyribonucleotide synthase (ATP) and Ribonucleic ligase.

Westaway S K, et al, J. Biol. Chem., 1988, 263(7), 3171–3176 describe the structure and function of the TRL1 gene from *S. cerevisiae*.

The present invention is based on the finding that TRL1 is an essential protein for the fungal species *Candida* and *Aspergillus*. This finding demonstrates the potential for developing fungal selective TRL1 inhibitors, which can kill invading fungal organisms while sparing the host of any detrimental effects. Prior to this invention, TRL1 has not been considered as a differential target for antifungal compounds.

SUMMARY OF THE INVENTION

The present invention relates to fungal tRNA ligase (hereinafter referred to as "TRL1") as a target for antifungal therapy, in particular, for antifungal therapy against *Candida* and *Aspergillus* species. The invention also relates to a method for screening or testing for potential antifungal compounds, e.g. small molecules, by determining whether a Candidate agent is capable of specifically inhibiting fungal ligase activity via a selective interaction with TRL1. The present invention describes the essential nature of TRL1 in *C. albicans*. It further describes the use of mechanism-based assays, with or without the use of a transformed eukaryotic organism with the TRL1 gene under the control of a heterologous promoter, to facilitate drug discovery.

Additionally, the invention relates to TRL1 inhibitor compositions and to methods for treating fungal infections, e.g. *Candida* and *Aspergillus* fungal infections, by administering to a host suffering from a fungal infection a therapeutically effective amount of a TRL1 inhibitor.

Definitions

In the context of this invention:

"Essential gene" is defined as a fungal gene necessary for growth on rich medium.

"TRL1 inhibitor" is defined as any compound that impairs TRL1 function in the fungus. A compound that impairs TRL1 function may be one that, modulates, e.g. inhibits, the expression or activity of TRL1, interacts with TRL1 or binds to TRL1. Furthermore, a compound that modulates the expression of TRL1 may interfere with the transcription of the gene encoding TRL1 or with the translation of mRNA encoding TRL1 in target organisms. It is desirable that the compound shows specificity for fungal over host TRL1. A therapeutically effective amount of a TRL1 inhibitor is one that is sufficient to inhibit partially or fully the ligase activity via TRL1 of the causative fungi.

"Fragment" is defined as a fragment of a TRL1 polypeptide e.g. as provided by accession numbers P43075, CA4962 or the Stanford orf6.7649, having at least 70%, more preferably it has at least 75%, at least 80%, at least 85%, at least 90%, at least 95% or at least 98% identity to the native polypeptide over the length of the fragment and which is at least ten amino acids long. An active fragment is one that retains the ability to carry out the TRL1 enzyme function.

"Function-conservative fragment" is defined as a TRL1 encoding sequence in which a given amino acid residue in the polypeptide has been changed without altering the overall conformation and function of the native polypeptide, including, but not limited to, replacement of an amino acid with one having similar physical and/or chemical properties (such as, for example, acidic, basic, hydrophobic, and the like) or polymorphisms.

"Fusion protein" unless otherwise specified, is defined as a TRL1 polypeptide, fragment or function-conservative fragment thereof fused via a covalent bond (e.g. a peptide bond), at optionally the N-terminus or the C-terminus, to an amino acid sequence of another protein (or portion thereof; preferably at least a 10, 20 or 50 amino acid portion of the protein). Preferably the polypeptide, or fragment thereof, is linked to the other protein at the N-terminus of the constant domain of the polypeptide.

"Growth" is defined as the normal growth pattern of fungi, i.e. the cell doubling time during the log phase of growth. For example, in rich media, wild-type *C. albicans* has a doubling time of approximately 60 minutes. Growth of the cells may be measured by following the optical density of cells in liquid media, where an increasing optical density indicates growth. Alternatively, growth can also be measured by colony formation from single cells on solid media plates.

"Viability" is defined as the ability of fungal cells to resume growth following a treatment of the cells that results in cessation of growth. One typical means by which viability is measured is by testing the ability of cells to form colonies on solid media plates.

DETAILED DESCRIPTION OF THE INVENTION

The invention provides TRL1 as a specific target for antifungal compounds.

The methods of the invention provide a facile and specific assay to screen compounds as potential antifungal compounds, in particular, as antifungal compounds against *Candida* and *Aspergillus* species.

Thus, the invention provides a method of screening or testing for antifungal compounds, e.g. against *Candida* or *Aspergillus* species, that impair TRNA ligase enzyme function (TRL1), comprising:

a) providing fungal TRL1, preferably *Candida* or *Aspergillus* TRL1;

b) providing one or more Candidate compounds;

c) contacting said TRL1 with said one or more Candidate compounds; and d) determining the interaction of the Candidate compound with said TRL1.

The screening method of the invention may be performed using techniques know in the art, e.g. the assay may comprise a growth inhibition assay, a binding assay or a translation inhibition assay. Binding assays include competitive binding assays, wherein the binding affinity of the Candidate compound is compared with that of a known enzyme substrate for TRL1, a preferred enzyme substrate is tRNA.

In the screening methods of the invention the Candidate compound or enzyme substrate may be labelled to allow easy quantitation of the interaction between the Candidate compound and the enzyme. Preferably the substrate is labelled e.g. using au radiolabel, such as but not limited to, $^{32}$P and the preferred substrate is tRNA.

TRL1 may be cloned or purified from fungi for use in in vitro binding, ligand binding or translation inhibition assays. Preferably, the TRL1 is from fungal pathogens of humans and animals, such as *Candida* or *Aspergillus* species. In a particular embodiment, TRL1 may comprise a fragment, a function-conservative variant, an active fragment or a fusion protein of TRL1.

TRL1 can be purified by techniques well known to those skilled in the art. Methods for polypeptide purification include, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the fungal target protein or against peptides derived therefrom can be used as purification reagents.

TRL1 can also be provided in a transformed eukaryotic organism under the control of a heterologous promoter. Such cells can be used in growth inhibition assays. Preferably, the eukaryotic organism is *C. albicans* or *S. cervisiae*. More preferably the organism is *C. albicans*. Briefly, a *C. albicans* strain is generated in which expression of the TRL1 gene can be tightly regulated. To do this the wild-type allele of the gene of interest is replaced with an allele that can be regulated by an exogenous agent. In general, nucleic acid manipulations and other related techniques used in practicing the present invention employ methods that are well known in the art, as disclosed in, e.g. Molecular Cloning, A Laboratory Manual (2nd Ed., Sambrook, Fritsch and Maniatis, Cold Spring Harbor) and Current Protocols in Molecular Biology (Eds. Ausubel, Brent, Kingston, More, Feidman, Smith and Stuhl, Greene Publ. Assoc., Wiley Interscience, NY, N.Y., 1997).

Thus, the invention also provides a modified eukaryotic cell(s) wherein the cell(s) expresses TRL1 under the control of a heterologous promoter. In one embodiment, the TRL1 may be heterologous or homologous. Preferably, the TRL1 is homologous.

The eukaryotic cell is preferably *C. albicans* or *S. cervisiae*, more preferably *C. albicans*.

In a specific embodiment, TRL1 may be expressed in a tetracycline-regulatable expression system. The tetracycline-regulatable expression system is an established tool for conditional expression of eukaryotic genes (Gossen M A, & H. Bujard, 1992, Proc. Natl. Acad. Sci. USA, 89:5547–5551; Nagahashi S, et al, 1997, Mol. Gen. Genet., 255:372–375; Nakayama H, et al, 1998, Microbiology, 144:2407–2415; Nakayama H, et al, 2000, Infect. Immun., December 68:12 6712–9). Such a system consists of two components derived from the Tn10 transposon of *Escherichia coli* (Hillen W, & A Wissmann, 1989, In Protein-nucleic acid interaction, vol. 10, Macmillan Press, London, United Kingdom, p. 143–162). The first component comprises a minimal promoter element downstream of a tetracycline operator sequence (tetO), which replaces the natural promoter of the target gene. The second component is a transactivator, that is a fusion protein comprising a transcriptional activation domain and the tetracycline repressor protein (TetR).

In the absence of tetracycline, TetR specifically binds to tetO as a dimer, resulting in the activation of transcription by recruiting the transactivator to the promoter. When tetracycline is present, it binds to the TetR repressor with high affinity and inhibits dimerisation, thereby preventing binding to tetO. Therefore, TRL1 gene expression is activated in the absence, and repressed in the presence, of tetracycline.

A synthetic tetracycline derivative, such as but not limited to, doxycycline can be used to control the expression of the TRL1 gene as described above.

The tetracycline-regulatable expression-system has several advantages over alternative systems. It was derived from a prokaryotic system so it is not anticipated to show pleiotropic effects (Gossen and Bujard, 1992), it can be used in an animal host (Nakayama H, et al, 1998, Microbiology, 144:2407–2415; Nakayama H, et al, 2000, Infect. Immun., December 68:12 6712–9), it is highly specific, and non-toxic.

Such modified cells may be used in screening methods. Thus, the invention also provides a method of screening or testing for Candidate anti-fungal compounds, e.g. against *Candida* or *Aspergillus* species, that impair TRNA ligase enzyme (TRL1) function, comprising; a) providing fungal TRL1, preferably *Candida* or *Aspergillus* TRL1, in a eukaryotic cell(s) that expresses TRL1 under the control of a heterologous promoter; b) providing one or more Candidate compounds; c) contacting said eukaryotic cell(s) with said one or more Candidate compounds; and d) determining the interaction of the Candidate compound with said TRL1 by assessing the effect on growth or viability of said cells.

The screening methods of the invention include both in vitro and in vivo methods. Candidate compounds which may be screened according to the methods of the invention include small molecules and peptides. The Candidate compounds may be synthetic compounds, a mixture of synthetic compounds, a crude preparation, a purified preparation or an initial extract of a natural product obtained from plant, microorganism or animal sources.

The invention also provides a compound identified by the screening methods described above, which impairs TRL1 function and is referred to herein as a "TRL1 inhibitor".

TRL1 inhibitors of the invention are useful as antifungal compounds. Thus, they may be used in the treatment and prevention of various fungal infections such as topical or mucosal (e.g. thrush and vaginal candidiasis) fungal infections, caused by e.g. *Candida* species, and for systemic fungal infections, caused by e.g. *Candida* and *Aspergillus* species, such as but not limited to *C. albicans*, *Aspergillus flavus* or *Aspergillus fumigatus*.

For the purposes of this invention, the medicament can be used in the curative or prophylatic treatment of fungal infections in humans and animals, especially domestic animals such as dogs, cats, horses etc.

In addition, the TRL1 inhibitors also find use in the curative or prophylatic treatment of fungal infections in subjects who are immunosuppressed e.g. as a result of a therapy (e.g. chemotherapy or radiotherapy), organ transplant or an infection (e.g. HIV).

In additional embodiments, therefore, the present invention provides:

i) the use of a TRL1 inhibitor as an anti-fungal agent.

ii) the use of a TRL1 inhibitor in the manufacture of a medicament for the treatment of fungal infections, such as topical or mucosal (e.g. thrush and vaginal candidiasis) fungal infections, e.g. caused by *Candida* species, and for systemic fungal infections e.g. caused by *Candida* and *Aspergillus* species, such as but not limited to, *C. albicans*, *Aspergillus flavus* or *Aspergillus fumigatus*.

iii) the use of a TRL1 inhibitor in the manufacture of a medicament for the treatment of fungal infections in a subject who is immunosuppressed, for example, as a result of a therapy (e.g. chemotherapy or radiotherapy), organ transplant or an infection (e.g. HIV).

iv) a method for the treatment or prevention of fungal infections in a host, such as topical or mucosal (e.g. thrush and vaginal candidiasis) fungal infections, e.g. caused by *Candida* species, and for systemic fungal infections, e.g. caused by *Candida* and *Aspergillus* species, such as but not limited to *C. albicans, Aspergillus flavus* or *Aspergillus fumigatus*, which comprises administering to the host a therapeutically or prophylactically effective amount of a TRL1 inhibitor.

v) a method for the treatment or prevention of fungal infections in a subject who is immunosuppressed, for example, as a result of a therapy (e.g. chemotherapy or radiotherapy), organ transplant or an infection (e.g. HIV) which comprises the step of administering to the subject a therapeutically or prophylactically effective amount of a TRL1 inhibitor.

In order to use TRL1 inhibitors in therapy (human or veterinary), they will normally be formulated into a pharmaceutical composition in accordance with standard pharmaceutical practice, e.g. by admixing the TRL1 inhibitor and a pharmaceutically acceptable carrier.

Thus according to a further aspect of the invention there is provided a pharmaceutical composition comprising a TRL1 inhibitor and a pharmaceutically acceptable carrier. The pharmaceutical compositions are particularly useful in the prevention or treatment of fungal infections, preferably, in the treatment of *Candida* or *Aspergillus* fungal infections.

TRL1 inhibitors may be administered to a host by any of the routes conventionally used for drug administration, for example they may be administered parenterally, orally, topically (including buccal, sublingual or transdermal) or by inhalation. The most suitable route for administration in any given case will depend on the particular TRL1 inhibitor, the infectious organism involved, the host, and the nature and severity of the disease and the physical condition of the host.

The TRL1 inhibitors may be administered in combination, e.g. simultaneously, sequentially or separately, with one or more other therapeutically active, e.g. antifungal, compounds.

The dosage to be administered of a TRL1 inhibitor will vary according to the particular TRL1 inhibitor, the infectious organism involved, the host, the severity of the disease, physical condition of the host, and the selected route of administration; the appropriate dosage can be readily determined by a person skilled in the art. For the treatment of fungal diseases in humans and animals, the dosage may range from 0.01 mg/kg to 750 mg/kg. For prophylactic use in human and animals, the dosage may range from 0.01 mg/kg to 100 mg/kg.

The compositions may contain from 0.1% by weight, preferably from 10–60% by weight, of the TRL1 inhibitor, depending on the method of administration.

Pharmaceutical compositions may be conveniently presented in unit dose forms containing a predetermined amount of TRL1 inhibitor per dose. Such a unit may contain for example but without limitation, 100 mg/kg to 0.1 mg/kg depending on the condition being treated, the route of administration and the age, weight and condition of the host. Preferred unit dosage compositions are those containing a daily dose or sub-dose, as recited above, or an appropriate fraction thereof, of the active ingredient.

It will be recognized by one of skill in the art that the optimal quantity and spacing of individual dosages of an agent of the invention will be determined by the nature and extent of the condition being treated, the form, route and site of administration, and the particular host being treated, and that such optimums can be determined by conventional-techniques. It will also be appreciated by one of skill in the art that the optimal course of treatment, i.e. the number of doses of an agent of the invention given per day for a defined number of days, can be ascertained by those skilled in the art using conventional course of treatment determination tests.

Dosage regimens are adjusted to provide the optimum desired response. For example, a single bolus may be administered, several divided doses may be administered over time or the dose may be proportionally reduced or increased as indicated by the exigencies of the therapeutic situation.

Pharmaceutically acceptable carriers for use in the invention may take a wide variety of forms depending, e.g. on the route of administration.

Compositions for oral administration may be liquid or solid. Oral liquid preparations may be in the form of, for example, aqueous or oily suspensions, solutions, emulsions, syrups or elixirs, or may be presented as a dry product for reconstitution with water or other suitable vehicle before use. Oral liquid preparations may contain suspending agents, for example sorbitol, methyl cellulose, glucose syrup, gelatin, hydroxyethyl cellulose, carboxymethyl cellulose; aluminium stearate gel or hydrogenated edible fats, emulsifying agents, for example lecithin, sorbitan monooleate, or acacia; water; non-aqueous vehicles (which may include edible oils), for example almond oil, oily esters such as glycerine, propylene glycol, or ethyl alcohol; preservatives, for example methyl or propyl p-hydroxybenzoate or sorbic acid; flavoring agents, preservatives, coloring agents and the like may be used.

In the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are generally employed. In addition to the common dosage forms set out above, TRL1 inhibitors may also be administered by controlled release means and/or delivery devices. Tablets and capsules may comprise conventional carriers or excipients such as binding agents for example, syrup, acacia, gelatin, sorbitol, tragacanth, or polyvinylpyrrolidone; fillers, for example lactose, sugar, maize-starch, calcium, phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated by standard aqueous or non-aqueous techniques according to methods well known in normal pharmaceutical practice.

Pharmaceutical compositions of the present invention suitable for oral administration may be presented as discrete units such as capsules, cachets or tablets, each containing a predetermined amount of the active ingredient, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or moulding, optionally with one or more accessory ingredients.

Compressed tablets may be prepared by compressing, in a suitable machine, the active ingredient in a free-flowing form such as a powder or granules, optionally mixed with a binder, lubricant, inert diluent, surface active or dispersing agent. Moulded tablets may be made by moulding, in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Compositions comprising a TRL1 inhibitor may also be prepared in powder or liquid concentrate form. Conventional water soluble excipients, such as lactose or sucrose, may be incorporated in the powders to improve their physical properties. Thus, particularly suitable powders of this invention comprise 50 to 100% w/w, and preferably 60 to 80% w/w of the combination and 0 to 50% w/w and preferably 20 to 40% w/w of conventional excipients. When used in a veterinary setting such powders may be added to animal feedstuffs, for example by way of an intermediate premix, or diluted in animal drinking water.

Liquid concentrates of this invention for oral administration suitably contain a water-soluble compound combination and may optionally include a pharmaceutically acceptable water miscible solvent, for example polyethylene glycol, propylene glycol, glycerol, glycerol formal or such a solvent mixed with up to 30% v/v of ethanol.

Pharmaceutical compositions suitable for parenteral administration may be prepared as solutions or suspensions of the TRL1 inhibitors in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include aqueous or non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. Extemporaneous injection solutions, dispersions and suspensions may be prepared from sterile powders, granules and tablets.

The compositions may be presented in unit-dose or multi-dose containers, for example in sealed ampoules and vials and to enhance stability, may be stored in a freeze-dried (lyophllized) condition requiring only the addition of the sterile liquid carrier, for example water for injections, immediately prior to use. The sterile liquid carrier may be supplied in a separate vial or ampoule and can be a solvent or dispersion medium containing, for example, water, ethanol, polyol (e.g. glycerol, propylene glycol and liquid polyethylene glycol), suitable mixtures thereof, and vegetable oils. Advantageously, agents such as a local anaesthetic, preservative and buffering agents can be included the sterile liquid carrier.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active ingredient. Thus, they may also comprise compatible conventional carriers and additives, such as preservatives, solvents to assist drug penetration, emollients in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5–10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

For applications to external tissues, for example the mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administration in the mouth include lozenges, pastilles and mouth washes.

Pharmaceutical compositions adapted for topical administration to the eye include eye drops wherein the active ingredient is dissolved or suspended in a suitable carrier, especially an aqueous solvent. They also include topical ointments or creams as above.

Pharmaceutical compositions suitable for rectal administration wherein the carrier is a solid are most preferably presented as unit dose suppositories. Suitable carriers include cocoa butter or other glyceride or materials commonly used in the art, and the suppositories may be conveniently formed by admixture of the combination with the softened or melted carrier(s) followed by chilling and shaping moulds. They may also be administered as enemas.

Pharmaceutical compositions adapted for vaginal administration may be presented as pessaries, tampons, creams, gels, pastes, foams or spray compositions. These may comprise emollients or bases as commonly used in the art.

All publications, including but not limited to patents and patent applications, cited in this specification are herein incorporated by reference as if each individual publication were specifically and individually indicated to be incorporated by reference herein as though fully set forth.

The following examples are to be construed as merely illustrative and not a limitation on the scope of the invention in any way.

EXAMPLES

Example 1

Expression of TRL1

The TRL1 ORF was cloned into pGex-6P-1 (Pharmacia Biotech) to enable expression as a 5' GST fusion protein. Host *E. coli* used were Rosetta(DE3)pLysS (Novagen) cells. Cells were grown at 37° C. to mid log phase (OD600=0.6) then cooled to 25° C. and induced with 0.3 mM IPTG for approximately 4 h.

Example 2

Purification of TRL1

E. coli cells from 10 L of culture were harvested by centrifugation at 6000×g for 10 min. The cell pellets were frozen at −80° C., thawed and resuspended in 250 ml of buffer A (20 mM Hepes (pH7.4), 5 mM DTT, 140 mM NaCl, 1 mM EDTA, 10% (v/v) glycerol, 0.02% (w/v) sodium azide, and a protease inhibitor cocktail consisting of 1 mM benzamidine, 1 μg ml$^{-1}$ each of pepstatin, antipain and leupeptin, 0.2 mM PMSF, Complete (Roche) and general protease inhibitor cocktail (Sigma).

The extract was sonicated in 3×10 s bursts to reduce viscosity. Triton X-100 was added to 1% followed by centrifugation at 75 000×g for 10 min. The supernatant was batch loaded onto 5 ml Glutathione Sepharose (Amersham Biosciences) at 4° C. with constant tumbling. The resin was extensively batch washed with phosphate buffer containing 0.5M NaCl then with buffer B (20 mM Hepes (pH 7.4), 1 mM DTT, 1 mM EDTA, 100 mM NaCl, 10% glycerol, 0.02% sodium azide). The resin was then packed into a disposable PD-10 column. GST-TRL-1 was eluted with buffer C (20 mM Hepes, (pH 8), 1 mM DTT, 1 mM EDTA, 10% glycerol, 0.02% sodium azide and 20 mM reduced glutathione).

Fractions containing GST-TRL-1 were pooled and incubated with PreScission protease (2.5 U/mg GST-TRL-1) (Amersham Biosciences) overnight at 4° C. The protein was then applied to a Mono Q column (HR5/5) linked to an AKTA FPLC system (Amersham Biosciences). TRL-1 was eluted using a linear 0–500 mM NaCl gradient and TRL-1 was eluted at approximately 300 mM NaCl.

Example 3

TRL1 Assay 3.1 Preparation of $^{32}$P Labelled tRNA Substrate

The complete C. albicans tRNA pro gene is amplified from CAF2-1 genomic DNA using an upstream primer containing the T7 promotor sequence and the downstream primer sequence.

T7 Promotor Sequence: TABLE-US-00001

```
TAATACGACTCACTATAGGGTCAATGGTGAAGTGGC (SEQ ID NO:1)
```

Downstream Primer Sequence: TABLE-US-00002

```
     GGGGTCAACCGGGAATCG         (SEQ ID NO:2)
```

The PCR product (300 ng) is used as a template for in vitro transcription for 3 h at 37° C. using MegaShortscript kit (Ambion) incorporating 1 μCi of [α$^2$P]ATP (Amersham). The template is degraded using Rnase free Dnase (Ambion) at 37° C. for 15 min and the tRNA substrate is precipitated by addition of 2× volumes of ethanol and resuspended in water to a concentration of 1 mg/ml.

3.2 Isolation of tRNA Endonuclease

The purification of tRNA endonuclease is loosely based on the method of Peebles C L, et al, (1983, Cell, 32(2) 525–36). C. albicans spheroplasts are prepared from 1.lamda. of CAF2-1 cells grown overnight in YEPD at 30° C. Pelleted cells are washed with 20 ml water and resuspended in 3 ml of zymolyase buffer (50 mM Tris-pH7.5, 10 mM MgCl$_2$, 1M Sorbitol, 30 mM DTT). After 15 min at room temperature the cells are pelleted and resuspended in 3 ml of zymolyase buffer plus 6 mg Zymolyase-100T (ICN). Following 90 mins incubation at 37° C. the spheroplasts are pelleted and washed 3 times and resuspended in 1.5 ml in zymolyase buffer.

Nuclei are isolated from the spheroplasts by pipetting drop by drop into 50 ml ficol buffer (18% ficol-400, 10 mM Tris pH7.5; 20 mM KCl; 5 mM MgCl$_2$; 3 mM DTT, 1 mM EDTA, protease inhibitor cocktail (Roche)) at 4° C. with continuous stirring. Unlysed cells and cell debris is removed by centrifugation at 3400×g (5 mins 4° C.) and the nuclei are pelleted by centrifugation at 20,000×g (20 mins 4° C.).

The nuclei are resuspended in 7.5 ml HSM (1M KCl, 100 mM Tris pH8, 10% glycerol, 2 mM EDTA, 5 mM Spermidine, 1 mM DTT, protease inhibitor cocktail (Roche)), pelleted at 20,000×g (20 min 4° C.) and resuspended in 7.5 ml LDM (20 mM Tris pH8, 10% Glycerol, 2 mM EDTA, 5 mM β-ME, 0.02% Triton X100). After 10 min at 4° C., the nuclei are pelleted by ultra-centrifugation (150,000×g 1 h 4° C.) and resuspended in 10 ml ME (20 mM Tris pH8, 10% glycerol, 5 mM β-ME, 1 mM EDTA,) plus 2% Triton X100 and 0.1M (NH$_4$)$_2$SO$_4$. After 30 min 4° C. the supernatant is clarified by ultra-centrifugation (150,000×g 1 h 4° C.)

The endonuclease is enriched by stepwise elution (20 ml ME, 0.9% Triton X100, 0.1M (NH$_4$)$_2$SO$_4$, followed by 20 ml ME, 0.9% Triton X100, 0.25M (NH$_4$)$_2$SO$_4$, followed by 20 ml ME, 0.9% Triton X100, 0.45M (NH$_4$)$_2$SO$_4$) of the supernatant applied onto a 10 ml Heparin-agarose (Sigma) column (pre-equilibrated with ME plus 0.9% Triton X100 and 0.1M (NH$_4$)$_2$SO$_4$). 2 ml fractions are collected, the endonuclease elutes in the 0.45M (NH$_4$)$_2$SO$_4$ fractions. The active fractions are pooled and dialysed overnight against 1.lamda. Storage buffer (20 mM Tris pH8, 0.2 mM EDTA, 0.5 mM DTT, 0.5% Triton X100, 35% Glycerol). The protein is concentrated (10×) by ultra-filtration (Vivaspin) and stored at −20° C. in aliquots.

3.3 Assay Conditions

The tRNA processing assay is based on the method of Greer C L, et al, (1983, Cell, 32(2) 537–46). Labelled tRNA substrate (100 ng) is spliced and ligated using 4 μg of TRL1 ligase and 10 μg of tRNA endonuclease in a 10 μl reaction containing 25 mM NaCl, 20 mM Tris pH7.6, 5 mM MgCl2, 2.5 mM Spermidine, 1 mM DTT, 0.4% Triton X100, 1 mM ATP, 0.1 mM GTP. The reaction is incubated at 30° C. for 1 h and stopped by adding 1 μl stop solution (100 mM EDTA, 0.2% SDS, 2 mg/mil Proteinase K). After 10 min at 50° C. an equal volume of gel loading buffer is added to the reaction (95% formamide, 0.5 mM EDTA, 0.025% xylene cyanol, 0.025% Bromophenol blue, 0.025% SDS) and the tRNA is denatured by heating at 95° C. for 2 min. The samples are loaded onto a 10% polyacrylamide TBE-Urea gel, and following electrophoresis at 100V, the tRNA bands on the gel are visualised by autoradiography.

Example 4

TRL1 as an Essential Gene Product 4.1 Construction of the Tetracycline-Regulatable Expression System C. albicans CAI8 is a suitable parental strain for all manipulations. The parental strain is constructed to constitutively express a codon-optimised tetracycline transactivator, consisting of TetR fused to the viral VP16 transcriptional activation domain (Gari E, et al, 1997, Yeast, 13:837–848), from the chromosomal enolase promoter (Mason A B, et al, 1993, J. Bacteriol., 175: 2632–2639). One copy of the target gene, TRL1, is disrupted in the transactivator expressing strain using the standard URA-blaster method (Fonzi W A & Irwin M Y, 1993, Genetics, 134:717–728). The promoter region of the other TRL1 allele is then replaced with the minimal promoter element containing the tetracycline operator sequence tetO. Both in vivo and in vitro this system enables strong induction and tight repression of TRL1 gene expression in the absence and presence, respectively, of the tetracycline analogue doxycycline.

4.2 In Vitro Validation Experiments

The essential nature of TRL1 may be determined by assessing the growth and viability of the *C. albicans* strain modified to include a tetracycline-regulatable TRL1-expression system as described above (section 4.1). A single fresh colony (grown at 30° C. in rich medium in the absence of tetracycline) is used to streak fresh plates containing synthetic complete medium minus uracil (SC-U) (Qbiogene), plus 2% agar, plus or minus 20 μg/ml doxycycline as indicated. Growth is scored after 2 days at 30° C. Impairment in the ability to form colonies would be expected under the conditions where TRL1 expression was repressed (i.e. in the presence of doxycycline).

Growth of the tetracycline-regulatable TRL1-expression system *C. albicans* strain in liquid SC-U medium may also be assessed. The inoculum is a 1:100 dilution of an overnight culture adjusted with PBS to an optical density at 600 nm=1 and stored at 4° C. Growth, at 25° C., plus or minus 20 μg/ml doxycycline, is measured at 30 min intervals over a 43 h time period or until the growth has noticeably reached a plateau. Growth curves are recorded in 96 well plates in a Wallac plate reader (600 nm, 25° C. heated stage, 2 mm orbital shaking pattern). Significantly reduced growth rates would be expected under the conditions where TRL1 expression was repressed (i.e. in the presence of doxycycline).

Example 5

TRL1 as an Essential Gene Product: In Vivo Validation Experiment—Murine Model of Systemic Infection with *C. albicans* Conditional Mutants Several reproducible animal models have been described including those of rat vaginal and oral Candidiasis (Calderone R A & Braun P C, 1991, Microbiol. Rev., 55:1–20). However, the most commonly used model is the murine model of hematogenously inoculated, disseminated Candidiasis (Ghannoum M A, et al, 1995, Infect. Immun., 63:4528–4530). In the murine disseminated model, a single dose of organism is inoculated via the tail vein. The end points for this model are survival of animals and tissue counts of *C. albicans* (generally the kidneys).

To further validate the essential nature of the TRL1 gene, the conditional mutants of *C. albicans* strains (as described in Example 4, section 4.1), wherein the TRL1 gene is under the control of a tetracycline repressible promoter, may be tested to determine whether they are attenuated in an immuno-competent murine model of infection (Ghannoum et al, 1995) as follows:

Initially the organisms are grown in the absence of DOX, since under these conditions they would express the TRL1 gene. These organisms are then used to inoculate two groups of 12 of mice. One group is treated with DOX, in which expression of the TRL1 gene is repressed, and the second group of mice is treated with water (control) wherein the gene continued to be expressed. The mice used are single sex BALB/c mice, Harlan, 4 weeks old and weighing between 19–22 g.

Infective doses of *C. albicans* are injected into the tail vein. The inocula are from saline-washed fresh stationary phase cultures grown in NGY medium [0.1% neopeptone, 0.4% glucose, 0.1% yeast extract] for 18–24 h at 30° C. Yeasts grown in this way have a viable count of $2\times10^7$ CFU/ml.+-.0.3×$10^7$ CFU/ml and can easily be adjusted to the desired concentration with saline. The concentration is checked by spectrophotometry and verified by viable counts. The volume injected is the same across the doses. An infective dose of $1\times10^6$ CFU/mouse is used. This infective dose has previously been shown to give a mean survival time of 5–7 days in BALB/c mice.

Animals are fed food and water ad libitum throughout the course of experiment. In the DOX-treated group (+DOX), mice are administered with DOX (2 mg/ml) dissolved in 5% sucrose solution as drinking water from 2 days before the inoculation of *C. albicans* cells. The mice are known to drink approximately 5 ml of sucrose solution every day. Under this regimen, the concentrations of DOX in serum, liver, and kidney are maintained at more than 2 mg/ml of serum, 8 mg/g of liver, and 10 mg/g of kidney, respectively (Nakayama H, et al, 1998, Microbiology, 144:2407–2415.) Percent survival is followed over 28 days with daily body weight monitoring. Differences between the effects of *C. albicans* with the TRL1 gene active (−DOX) or repressed (+DOX) in vivo are monitored by mouse survival, kidney burdens of viable fungi, and changes in body weight relative to baseline.

Sequence CWU 1

2 1 36 DNA *Homo sapiens* 1 taatacgact cactataggg tcaatggtga agtggc 36 2 18 DNA *Homo sapiens* 2 ggggtcaacc gggaatcg 18

---

The invention claimed is:

1. A method of screening or testing for Candidate antifungal compounds that impair tRNA ligase enzyme (TRL1) function, comprising: a) providing *Candida albicans* TRL1; b) providing one or more Candidate compounds; c) contacting said TRL1 with said one or more Candidate compounds; and d) determining the interaction of the Candidate compound with said TRL1.

2. A method according to claim 1 wherein the TRL1 comprises a fusion protein of TRL1.

* * * * *